(12) United States Patent
Hammerman

(10) Patent No.: US 7,384,630 B2
(45) Date of Patent: Jun. 10, 2008

(54) CHIMERIC PANCREAS

(75) Inventor: Marc R. Hammerman, St. Louis, MO (US)

(73) Assignee: Washington University, St. Louis, MO (US)

( * ) Notice: Subject to any disclaimer, the term of this patent is extended or adjusted under 35 U.S.C. 154(b) by 708 days.

(21) Appl. No.: 10/395,552

(22) Filed: Mar. 24, 2003

(65) Prior Publication Data

US 2003/0198628 A1 Oct. 23, 2003

Related U.S. Application Data

(60) Provisional application No. 60/367,181, filed on Mar. 25, 2002.

(51) Int. Cl.
*C12N 5/08* (2006.01)
(52) U.S. Cl. .............. 424/93.7; 435/1.1; 514/866
(58) Field of Classification Search ............. 424/556
See application file for complete search history.

(56) References Cited

U.S. PATENT DOCUMENTS

| 5,538,713 | A | * | 7/1996 | P eault | 424/9.2 |
| 5,593,673 | A | | 1/1997 | Dinsmore | |
| 5,804,178 | A | * | 9/1998 | Vacanti et al. | 424/93.7 |
| 2002/0168371 | A1 | * | 11/2002 | Awwad | 424/178.1 |
| 2003/0031652 | A1 | * | 2/2003 | Hering et al. | 424/93.21 |

FOREIGN PATENT DOCUMENTS

WO WO 01/39784 6/2001

OTHER PUBLICATIONS

Hullett et al., Diabetes 38: 448453 (Apr. 1989).*
Groth et al., The Lancet344: 1402-1404 (Nov. 19, 1994).*
Rogers et al., Transplant Immunology 14: 67-75 (2005).*
Stedman's Medical Dictionary, 2d Edition, definition of the term "primordium", 2000.*
Rogers et al, "Intraperitoneal Transplantation of Pancreatic Anlagen" ASAIO Journal, 2003, vol. 49, No. 5, pp. 527-532.*
Hegre et al, "Syngeneic Transplantation of the Fetal Rat Pancreas IV. Dissociated Versus Whole Organ Implantation" Metabolism, 1979, vol. 28, No. 2, pp. 157-162.*
Hammerman, "Organogenesis of Endocrine Pancreas from Transplanted Embryonic Anlagen," Transplant Immunology, 2004, pp. 249-258, vol. 12.
Rogers et al.,Islet cell engraftment and control of diabetes in rats following transplantation of pig pancreatic anlagen, Am. J. Physiol (2004) 286, E502-509.
Eloy et al., Chick Embryo Pancreatic Transplants Reverse Experimental Diabetes of Rats, J. Clin. Invest. (1979) 64, 361-373.

* cited by examiner

Primary Examiner—Leon B. Lankford, Jr.
Assistant Examiner—Allison M. Ford
(74) Attorney, Agent, or Firm—Sonnenschein Nath & Rosenthal LLC

(57) ABSTRACT

Novel methods, tissues and compositions for increasing the pancreatic mass of a mammalian recipient including harvesting immature pancreatic tissue from a mammalian donor and transplanting said tissue into the peritoneal cavity of a mammalian recipient under conditions that allow the pancreatic tissue to become vascularized and mature, thereby developing a functioning chimeric, endocrine pancreas that produces at least insulin in the recipient. The invention also includes mammalian immature pancreatic tissue adapted for transplantation into the peritoneal cavity of a mammalian recipient for increasing the pancreatic mass of the mammalian recipient as well as methods and compositions for treatment of the pancreatic tissue, recipient immunosuppression and recipient co-stimulatory blockade.

15 Claims, 12 Drawing Sheets

CHIMERIC PANCREAS

RELATED APPLICATIONS

This application claims the benefit of U.S. provisional application Ser. No. 60/367,181, filed Mar. 25, 2002 and incorporated herein as if restated here in full.

GOVERNMENT RIGHTS IN THE INVENTION

This invention was made with the support of government grant R01 DK53497 from the National Institutes of Health. The government of the United States of America has certain rights in this invention.

FIELD OF THE INVENTION

The present invention relates to the field of biotechnology, in particular, methods, tissues and compositions for increasing the pancreatic mass of a mammalian recipient.

BACKGROUND OF THE INVENTION

Idiopathic or primary diabetes mellitus is a chronic disorder of carbohydrate, fat, and protein metabolism characterized in its fully expressed form by an absolute or relative insulin deficiency, fasting hyperglycemia, glycosuria, and a striking tendency toward development of atherosclerosis, microangiopathy, nephropathy, and neuropathy. Underutilization of glucose is characteristic of all diabetic patients, but only some have a clearly defined severe insulin deficiency resulting from a loss of beta cells. The large remainder of diabetic patients suffers from some impairment of insulin secretory response associated with a marked resistance to insulin in the peripheral tissues.

The phrase "idiopathic diabetes mellitus" embraces a heterogeneous group of disorders having in common the above-described characteristics. At least two major as well as several less common variants of the disease have been identified. One major variant, insulin-dependent diabetes mellitus (IDDM) (Type I), accounts for about 10% of diabetics. A second major variant, non-insulin-dependent diabetes mellitus (NIDDM) (Type II) represents the remaining 90% of all diabetic patients. Absent regular insulin replacement therapy using exogenously produced insulin and/or careful monitoring of the diet of diabetic patients, such patients experience a wide range of debilitating symptoms, some of which can progress into coma and ultimately death.

In mammals, the pancreas is the primary organ responsible for the maintenance of normoglycemia. Generally, the mature mammalian pancreas develops from 2 pancreatic buds (or anlagen) called the dorsal pancreas and the ventral pancreas. These anlagen will fuse during development to form the pancreas although the dorsal anlage arises first and generates most of the pancreas. The ventral anlage arises beside the bile duct and forms part of the head and uncinate process of the pancreas.

The mature pancreas has both exocrine (digestion) and endocrine (hormonal) functions. The exocrine function includes secreting enzymes to aid in digestion. The pancreatic hormonal function includes secreting at least insulin and glucagon, two hormones which together help regulate blood glucose levels. Within the endocrine pancreas, it is the beta cells, which are organized into areas called islets of Langerhans, that create and excrete insulin. Glucagon is secreted by alpha cells within the islets of Langerhans.

Many attempts have been made to replace pancreatic mass and/or function in diabetic recipients through surgical methods. For example, transplantation of digested and isolated islets of Langerhans derived from human cadaveric pancreas to immunosuppressed diabetic humans is an established but experimental means to treat diabetes mellitus. Given existing technology, a major limitation of this technique is the insufficient supply of human pancreatic tissue available for transplantation. In addition, islet tissue may be lost or degraded during the digestion and isolation procedures as well as after transplantation as only a fraction of the transplanted islets engraft in the host. Mass increase of the beta cells within the islets may also be sub-optimal as such transplants exhibit limited potential for expansion of the beta cell mass. Moreover, the immunosuppression and related issues involved in any cadeveric transplantation can be quite significant.

Isotransplantation of whole immature, fetal rat pancreas to rat subcapsular kidney space, anterior eye chamber, testis, subcutaneous pocket, third ventricle, and cheek pocket, are also known in the art. Such work also includes the effect of insulin treatments on the growth and differentiation of the transplanted tissue.

Transplantation of collagenase digested and isolated mature rat and hamster islets into hamster skin folds and striated muscle tissue wherein the isolated islets revascularize is also known. At least two immunosuppressive regimens, cyclosporineA (CsA) and 15-deoxyspergualin (DOS), are known to be useful for such xenografts. Similarly, it is known to inject dispersed developing rat pancreas (minced, disassociated and collagenase digested) into the peritoneal cavity or subcapsular site of the kidneys of alloxan diabetic rats, to reverse, at least temporarily, their diabetes.

Isolated islet clusters of fetal porcine pancreas have also been used as a xenogeneic transplant for human diabetic patients. Thus, it is known to isolate pancreatic islets from pig fetuses and inject the islets into a vein of a human diabetic patient. A notable problem with such procedures is the necessity for maintenance immunosuppression with cyclosporine, prednisolone and azathioprine. An additional problem is that such grafts do not help the recipient attain control for levels of circulating glucose.

The shortcomings of the prior methods are significant. Dispersed or cluster cell methods require large amounts of donor tissue and usually multiple donors per recipient. Strong immune suppression is also needed to help avoid acute rejection of the transplanted cells. Moreover, given the dispersed form of cellular and cluster transplants, the actual implantation may be difficult to control and no single, developing chimeric organ is ever created. Among other differences, prior transplantations of whole adult or immature pancreatic tissue have utilized tissue substantially more developed than that of the present invention and have not focused on the peritoneum as the transplant site. As a result, the prior techniques exhibit increased risk of hyperacute and/or acute vascular rejections as well as the potential for unwanted and unnecessary development of exocrine pancreatic function. Only the present invention provides for the development of a newly vascularized, chimeric pancreatic organ with endocrine, but not exocrine, function while substantially avoiding or reducing at least hyperacute and acute-vascular transplant rejection.

The chimeric pancreas of the present invention substantially increases or is at least capable of increasing in functional mass within the host to establish at least near normal levels of glycemia within the host. This is reflected by at least: 1) the absence of insulin in immature pancreatic tissue transplants at the time of implantation and the presence of such secreted insulin in developing islets two weeks after transplantation; and 2) the approximately 30 day delay between transplantation of immature pancreatic tissue in streptozotocin diabetic rats and the resulting euglycemia of the host as the tissue develops and matures.

Accordingly, and in light of the failure of any of the prior methods to lead to an effective treatment for diabetes mellitus in humans, there is a need to develop novel methods, tissues, and compositions for transplanting immature pancreatic tissue into mammalian recipients to increase the pancreatic mass of the recipient.

SUMMARY OF THE INVENTION

One embodiment of the present invention is directed to a novel method for increasing the pancreatic mass of a mammalian recipient comprising harvesting immature pancreatic tissue from a mammalian donor and transplanting said tissue into the peritoneal cavity of a mammalian recipient under conditions that allow the pancreatic tissue to become vascularized and mature, thereby developing a functioning chimeric, endocrine pancreas that produces at least insulin in the recipient.

Another embodiment of the present invention is mammalian immature pancreatic tissue adapted for transplantation into the peritoneal cavity of a mammalian recipient for increasing the pancreatic mass of the mammalian recipient.

Another embodiment of the present invention is recipient immunosuppression compositions and methods to immunosuppress the recipient of a transplant of immature pancreatic tissue into the peritoneal cavity of the mammalian recipient to decrease the chance of rejection of the transplanted tissue.

Another embodiment of the present invention is recipient co-stimulatory blockade compositions and methods for co-stimulatory blockade of the immune response of the recipient of a transplant of immature pancreatic tissue into the peritoneal cavity of the mammalian recipient to decrease the chance of rejection of the transplanted tissue.

Another embodiment of the present invention includes compositions and methods for treatment of the harvested tissue for enhancing the post-implantation growth and development of the tissue. This embodiment may comprise incubating the isolated mammalian immature pancreatic tissue adapted for transplantation into the peritoneal cavity of a mammalian recipient with growth factors prior to implantation for enhancing the post-transplantation growth and development of the transplanted tissue in the mammalian recipient.

In each embodiment herein, the immature pancreatic tissue may comprise fetal mammalian pancreatic tissue which, at the time of harvesting, is substantially unvascularized by the donor and substantially free of antigen presenting cells.

A goal of the present invention is to provide methods, tissues and compositions for transplanting immature mammalian pancreas tissue into mammalian recipients to increase the pancreatic mass of the recipient.

Other aspects and features will be in part apparent and in part pointed out hereinafter.

DESCRIPTION OF THE DRAWINGS

FIG. 6A is an H&E stained section;

FIG. 6B is a control stained section;

FIGS. 6C and 6D are anti-insulin stained sections;

FIG. 12A shows a control serum;

FIG. 12B shows the use of an anti-insulin antibody which highlights the insulin producing cells; and FIG. 12C shows a combined Gomori stain which highlights the pancreatic islets (identified by arrows in each frame).

DETAILED DESCRIPTION

Figure 1:
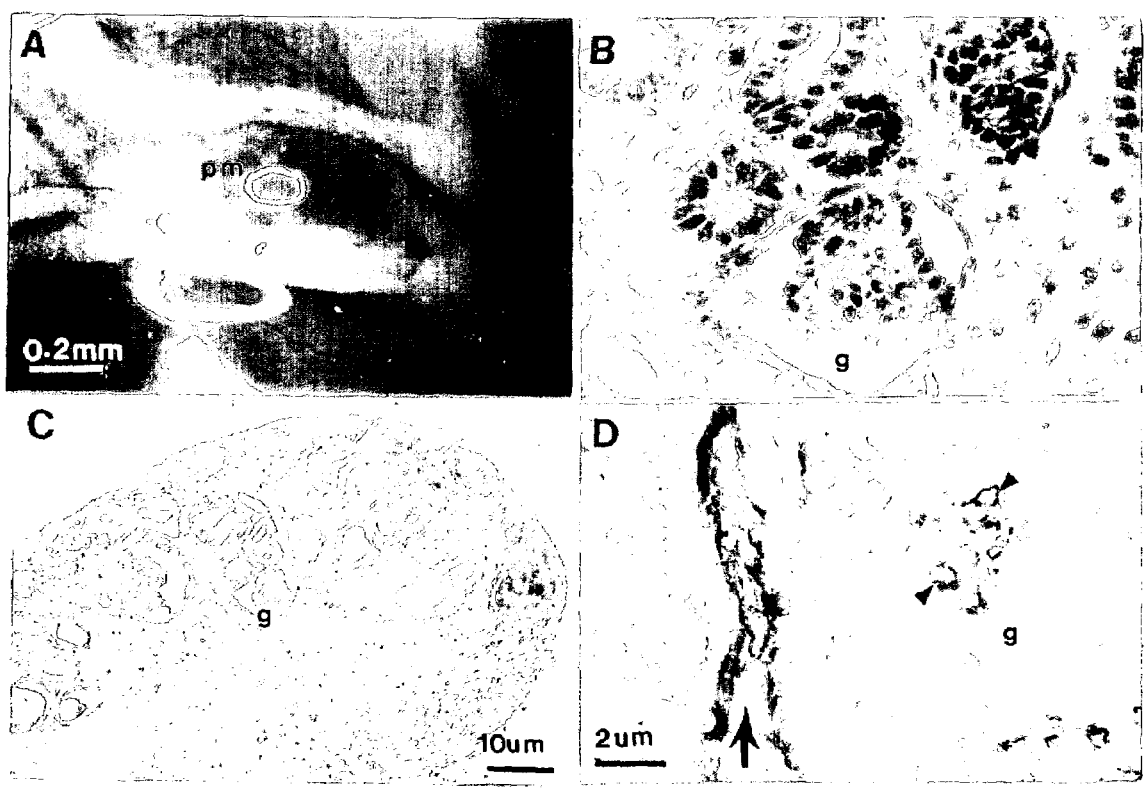
FIG. 1A is an embryonic day (E) 28 pig metanephros (pm) 14 days post-implantation into the mouse omentum.
FIGS. 1B and 1C show hemotoxylin and eosin ("H&E")-stained sections of paraffin embedded pig metanephroi 14 days post-implantation into the mouse omentum. Glomeruli are labeled (g)
FIG. 1D illustrates a paraffin-embedded section of a developed pig metanephros 14 days post-implantation into the mouse omentum stained with mouse-specific endothelial cell marker anti-CD31. Positive-staining (CD 31-positive) vascular structures of mouse origin (arrow and arrowhead) are delineated within the pig metanephros; magnifications are shown for A & B(A) and for C and D.

The following detailed description is provided to aid those skilled in the art in practicing the present invention. The description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

One embodiment of the present invention is directed to a novel method for increasing the pancreatic mass of a mammalian recipient comprising harvesting immature pancreatic tissue from a mammalian donor and transplanting said tissue into the peritoneal cavity of a mammalian recipient under conditions that allow the pancreatic tissue to become vascularized by vessels originating from the host and mature, thereby developing a functioning chimeric, endocrine pancreas that produces at least insulin in the recipient. The immature pancreatic tissue may comprise immature mammalian pancreatic tissue which, at the time of harvesting, is at least substantially unvascularized by the donor and at least substantially free of antigen presenting cells.

A preferred embodiment comprises harvesting immature pancreatic tissue from at least one embryonic mammalian donor, preferably a porcine donor, said tissue comprising at least one substantially non-vascularized dorsal, ventral or combined dorsal and ventral pancreas anlage substantially free of antigen presenting cells. Said tissue is transplanted into the peritoneal cavity of a diabetic human patient at a site adjacent to branches of the superior mesenteric artery. Post-transplantation, said tissue vascularizes and matures, thereby developing a functioning chimeric, endocrine pancreas that produces at least insulin in the recipient. Said preferred method may also comprise administering immunosuppression or a co-stimulation blockade to the recipient's immune system to aid in the prevention of rejection of the transplanted tissue.

Said preferred method may also comprise methods and compositions for treating the tissue to enhance the post-implantation growth and development of the tissue.

Suitable mammalian donors may be selected for compatability with a host based on known transplant protocols as well as various factors including similar physiology, organ size, antigen profiles, donor availability and similarity of pancreatic endocrine function.

A preferred mammalian donor for a human recipient may be swine bred to be pathogen free and possibly transgenic for some human proteins such as decay accelerating factor and CD59, or alpha-gal transferase deficient swine. Pigs are preferred xenogeneic donors for human recipients because, among other factors, of their comparable organ size and their general availability as donors. Moreover, the processes of glucose homeostatis and regulation of insulin secretion are very similar in swine and humans.

In addition, human immature pancreatic tissue may be preferred for allogeneic transplantation into human recipients.

In a preferred embodiment, the immature pancreas tissue may comprise at least one embryonic dorsal or pancreatic anlage that is substantially non-vascularized within the donor at the time of the harvest. Said tissue may further comprise both dorsal and ventral anlagen, one or more such anlagen, whole pancreata (both dorsal and ventral anlagen or fused anlagen), or such tissue from one or more donors. Although it is preferred to use whole anlagen, it is within the scope of the immature pancreatic tissue of the present invention to include non-digested, non-disassociated portions of such tissue as well.

The immature pancreatic tissue may be harvested from at least one donor at a suitable stage of development, namely, immediately before or within days after the dorsal and ventral anlage become fused and prior to vascularization and the creation and distribution within the tissue of antigen-presenting cells by the donor. Preferably, the immature pancreatic tissue is harvested as soon after the immature pancreas begins formation and can be dissected free from the donor tissues and prior to the presence of blood vessels that either originate within the pancreas or from outside the pancreas. Harvesting prior to vascularization is particularly preferred as mature antigen presenting cells will not yet have formed in the developing embryos from which the pancreatic anlagen are obtained or if they have formed, will not have migrated into the avascular pancreatic anlage. At this time, the immature pancreatic tissue may be considered free or at least substantially free of antigen-presenting cells.

Tissue harvested too late in the development of the pancreas, for example, tissue having visible blood vessels, may contain more antigen-presenting cells and cell-surface antigens and thus present more of a threat of rejection by the recipient. Tissue harvested at the preferred timing of development and vascularization will be substantially free of antigen presenting cells which means that the chance of at least hyperacute and acute vascular rejection in non-isograft transplants is greatly reduced when compared to transplants of vascularized grafts or those containing antigen presenting cells.

The specific developmental stage for harvesting the pancreatic tissue will vary depending upon the species of donor. In rats, the pancreas forms on day 11-12 of a 22-day gestation period with the preferred time for immature pancreatic tissue harvest being between about day 12 to about day 13. In mice, pancreas formation is around day 10-11 of a 19-day gestation period and preferred harvest is from about day 11 to about day 12. In pigs, the pancreas forms on days 16-18 of a 115 day gestation period with preferred harvest being from about day 20 to about day 38 with a more preferred period for harvest being about day 25 to about day 35 and a most preferred harvest date being about day 29. In humans, the pancreas forms on days 31-40 of a 270 day gestation period with preferred harvest being from about day 40 to about day 50 or early in the first trimester of pregnancy.

In one aspect of the present invention, the recipient is a mammal and can be of any age. A preferred recipient is a human, and more preferably it is a human patient with Type II or Type I diabetes. In another preferred embodiment, such recipient exhibits reduced functional pancreatic mass as a result of suffering from one of the above-mentioned diseases.

A preferred method comprises implanting immature pancreatic tissue comprising at least one whole pancreatic anlage of an embryonic mammalian donor into the peritoneal cavity of a mammalian recipient under conditions that allow the immature pancreatic tissue to become vascularized and mature, thereby developing a functioning endocrine chimeric pancreas that produces at least insulin in the recipient. The pancreatic tissue is implanted into the peritoneal cavity of the recipient using methods known to one of ordinary skill in the art.

In one embodiment, the pancreatic tissue is implanted near the omentum of the recipient adjacent to a branch of the superior mesenteric artery, and preferably it is implanted into a pouch of the omentum. Immature pancreatic tissue transplanted using the techniques described herein is initially non-vascularized and, therefore, grows and becomes vascularized at least in part by the recipient's blood vessels, developing at least one chimeric, endocrine pancreas. The chimeric pancreata are characterized by the formation of mature and functioning islets of Langerhans, which can produce and externalize at least insulin and possibly, glucagon and somatostatin.

Vascularization by the recipient may facilitate the acceptance of transplanted xenogeneic tissue. More specifically, the lack of existing vascularization in the transplant and the lack of vascular anastomosis between the transplanted tissue and the recipient at the time of the transplant, aids in the avoidance of at least hyperacute and acute vascular rejection of the tissue. Thus, xenogeneic transplants of the present invention are able to avoid two of the more serious types of organ rejection and vascularize and develop into functioning chimeric organs within the hosts.

For allogeneic transplantation of the immature pancreatic tissue, any embryonic anlage(n) may be transplanted into a recipient of the same species who is in need of such transplant. If desired, MHC (major histocompatibility complex) haplotype matching between a donor and a recipient may be performed using any method known in the art, such as the mixed lymphocyte reaction.

Suitable conditions for vascularization and maturity of the chimeric endocrine pancreas of the present invention may also include the use of pre or post-operative methods and compositions to facilitate the development and functioning of the transplanted tissue and to prevent rejection of the transplant. In isogeneic and some cases of allogeneic transplantation, there may be no host rejection of the transplanted pancreatic tissue, therefore, immunosuppression and/or co-stimulation methods and compositions may be avoided. Moreover, the inventive immature pancreatic tissue may be adapted for use in the present invention by treatment with growth factors and other compounds and compositions to enhance its growth and development within the host, its development of insulin producing beta cells within the host, and to reduce the likelihood of transplant rejection.

Another embodiment of the present invention is recipient co-stimulatory blockade compositions and methods (see Example Regimen 1 and Regimen 2) for the transplantation of immature pancreatic tissue into the peritoneal cavity of a mammalian recipient for increasing the pancreatic mass of the mammalian recipient. As is known, CD4+ T cells play a major role in non-vascularized, acute, T-cell mediated rejection of allo- and xeno-grafts. Thus, combating such rejection by targeting the activation and/or function of CD4+ T cells by blocking co-stimulation of the recipient's T-cell response has proven effective in the present invention. Suitable immunomodulatory agents and methods that target and downmodulate the host's T-cell response to the transplanted tissue may be used and are contemplated in the present invention.

A first such method comprises compositions of CTLA4Ig (Genetics Institute, Cambridge Mass.) and anti-CD2 (Pharmingen, San Diego Calif.) which may be administered to the recipient before, during and after transplantation.

A second method of co-stimulatory blockade comprises compositions of anti-CD11a (Pharmingen, San Diego Calif.), anti-CD45RB (Clone 23G2, Pharmingen, San Diego Calif.) and anti-CD154 (Clone MR1, Pharmingen, San Diego Calif.) which may also be administered before, during and after transplantation.

In at least the case of xenogeneic transplantation, the invention may include immunosuppression methods and compositions for the recipient. This is usually done by immunosuppressing the recipient after the implantation. Cyclosporine A (CSA) treatments may provide sufficient immunosuppression to prevent rejection of the donor tissue. CSA treatment methods to prevent transplant rejection are known in the medical field. Local immunosuppression techniques are described by Gruber (1992), *Transplantation* 54:1-11. In U.S. Pat. No. 5,560,911, antibodies directed against idiotypes on naturally occurring human anti-animal antibodies are disclosed for use in inhibiting xenograft rejection. Anti-lymphocyte globulins are also known for prevention of transplant rejection (Lacy et al. (1981), *Diabetes* 30:285-291). As an alternative to immunosuppression, the implanted pancreas can be treated prior to implantation to reduce its antigenicity. Exemplary approaches to the reduction of immunogenicity of transplants by surface modification are disclosed by Faustman WO 92/04033 (1992).

In a preferred aspect of the invention, the immunosuppression composition given to the recipient receiving the immature pancreatic tissue will be based on the use of those immunosuppressive agents which have proven to be less diabetogenic. For example, the use of corticosteroids, cyclosporine A, or tacrolimus may be limited for the transplantation purposes described herein. An example of a successful immunosuppressive treatment may be based on the one used in the Edmonton method (Shapiro et al, 2000), which requires long-term high dose Sirolimus (non-diabetogenic), long-term low-dose Tacrolimus (diabetogenic) and short term Daclizumab.

Immature pancreatic tissue may be adapted for transplantation by preparing it for or maintaining it in the cold (approximately 4 Celsius) prior to transplantation but after harvesting. The invention may further comprise adapting the pancreatic tissue for transplantation by contacting the isolated mammalian immature pancreatic tissue with growth factors, growth medium, and other compounds and compositions to enhance the post-implantation growth and development of the tissue. One such composition may comprise hepatocyte growth factor (preferably 10-9 M) and VEGF (preferably 5 ug/ml) in HamsF12:Dulbecco's modified Eagles medium (preferably 50 to 100 ul of a 50:50 mix) post-harvest and prior to implantation. In a preferred embodiment, the tissue is incubated with said composition for ¾-3 hours at 4 degrees Centigrade.

Harvested tissue may be treated with various growth factors and growth promoting agents, or combinations thereof, to enhance transplant development. For example, contacting harvested tissue with hepatocyte growth factor (HGF) may enhance beta cell proliferation and increases islet mass in vivo. Similarly, vascular endothelial growth factor (VEGF) may be used to increase vascularization of pancreatic islets. Other growth factors that may be employed to design and implement enhanced development and maturation protocols include, among others: the epidermal growth factor (EGF) family ligands, which can regulate the lineage determination of endocrine cells within pancreatic anlagen maintained in organ culture; betacellulin (BTC), which favors beta cell differentiation; and Neuregulin (NRG-4), which affects the development of somatostatin-producing delta cells; retinoid antagonists, which inhibit acinar differentiation in vitro; members of the transforming growth factor family (TGFs), growth factors (IGFs), gastrin, activin A, and members of the fibroblast growth factor (FGF) family.

Enhanced development of the transplant, specifically the beta-cells, may be enhanced by post-surgical administration of insulin, particularly exogenous insulin, to the recipient. In a preferred embodiment, the invention includes the step of administering exogenous insulin to the patient post-transplantation to enhance the development of the transplanted tissue.

After a sufficient period of development, it is evident that the inventive transplanted tissue is capable of excreting insulin. By virtue of the transplantation of the tissue into the peritoneal cavity, the excreted insulin is released directly into the portal system of the recipient. Hence, transplantation of the immature pancreatic tissue using the inventive methods and compositions contributes to the increased functional endocrine mass of the recipient.

Figure 7:
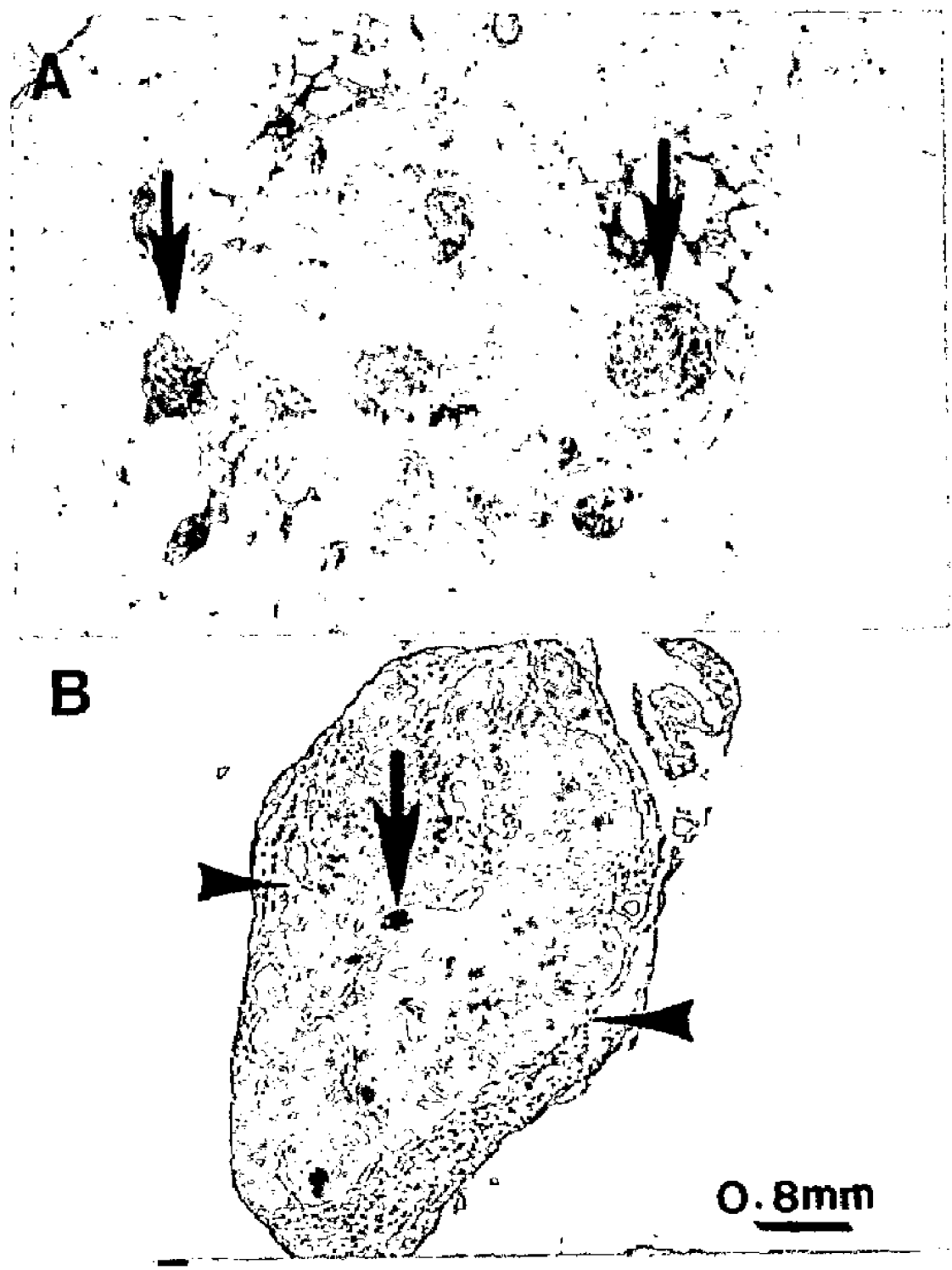
FIG. 7A shows sections of pancreatic tissue recovered fifteen weeks post-transplantation, islets are shown by arrows.
FIG. 7B shows, for comparison, sections of dorsal pancreatic anlage from a newborn rat, acinar cells are shown by arrowheads while islets are shown by arrows.

Also, after a sufficient period of development, it is evident that exocrine pancreatic tissue is absent from the chimeric pancreas. Instead, it consists of islets of Langerhans and stromal tissue as shown in FIG. 7. Therefore, there is no need to devise methodology to drain exocrine pancreatic secretions from the chimeric pancreas.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the example.

Co-Stimulatory Blockade Regimens for Porcine to Mouse Transplant

Regimen 1

In this example, developing porcine metanephros tissue (developing kidney anlagen) was transplanted from a donor pig into a mouse recipient. The treatment method involved administering to the Recipient C57B1/6J mice, a composition of CTLA4Ig, 0.5 mg/day on days 2 and 1 prior to implantation, on the day of implantation and on day 5 post-implantation; and a composition of anti CD2, 0.5 mg on the day of implantation and on days 3, 7 and 10 post-implantation. Shown in FIG. 1A is a pig metanephros (m) 14 days post-implantation into the mouse omentum. H&E-stained sections of paraffin embedded metanephroi are shown in FIG. 1B and C. Glomeruli are labeled (g). FIG. 1D illustrates a paraffin-embedded section stained with mouse-specific anti-CD31 (6). A blood vessel (arrow) and glomerular capillary loops (arrowheads) are delineated in the pig metanephros. These vessels and loops are of mouse origin (stain + for mouse-specific anti-CD31). Glomeruli (g) are labeled. Thus, it is evident that the transplanted porcine tissue was not rejected in the rat recipient and, in fact, developed and became vascularized by the recipient during its development.

Regimen 2

Figure 2:
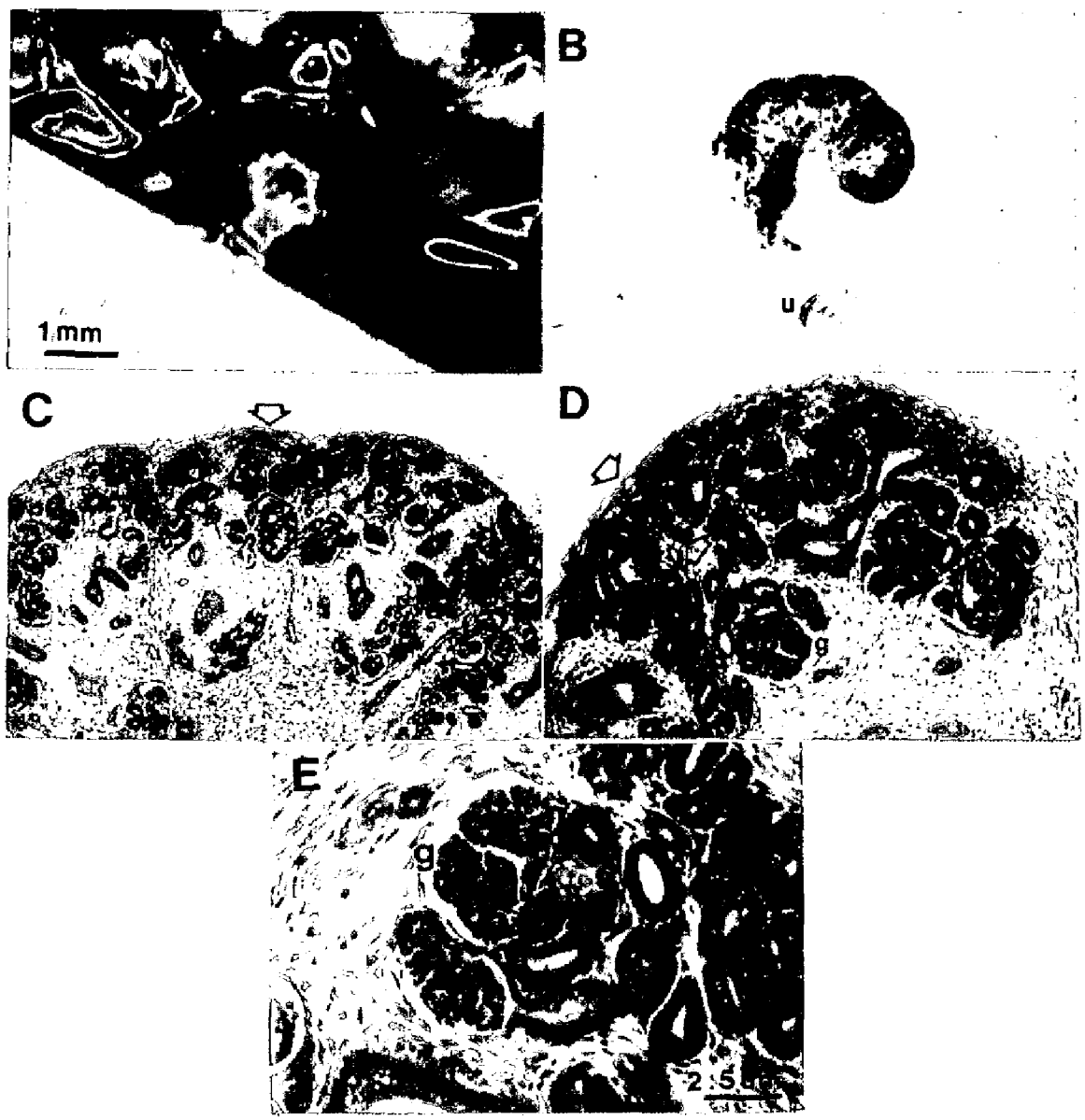
FIG. 2A is a pig metanephros (m) 14 days post-implantation into a mouse omentum.
FIGS. 2B-2E show H&E-stained sections of the implanted metanephros. Glomeruli are labeled (g), magnifications are shown for A & B (B), C, D and E.

This method and composition are also exemplified by a porcine to mouse metanephros transplant. Recipient mice were treated with anti CD11a, 0.2 mg iv on the day of implantation and on days 0, 1, 7, and 14 post-implantation; anti CD45RB, 0.2 mg iv on days 3 and 2 prior to implantation, 0.3 mg on day 1 prior to implantation and 0.1 mg on the day of implantation and days 1-10 post implantation; and anti CD 154, 0.25 mg iv on the day prior to implantation, the day of implantation and on days 2 and 4 post-implantation. Shown in FIG. 2A is the pig metanephros (m) 14 days post-implantation into the mouse omentum. H&E-stained sections are shown in FIGS. 2B-E. A ureter (u) is labeled in FIG. 2B. The nephrogenic zone (developing nephrons) is delineated (arrows FIGS. 2C and D). A glomerulus (g) is labeled in FIGS. 2D and 2E. Again, the post-implantation figures establish that the metanephros vascularized and developed within the host without rejection.

Figure 3:
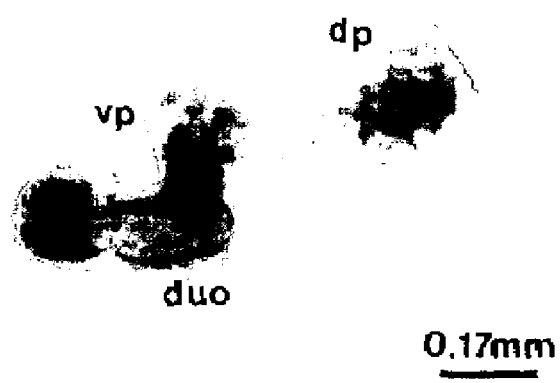
FIG. 3A is a photograph of a section of duodenum (duo) from an E12.5 Lewis rat embryo. The dorsal pancreas anlage (dp) and ventral pancreas anlage (vp) are labeled.
FIG. 3B is a H&E stained section of the dp and vp with the duodenum removed.
FIG. 3C is a higher-power view of the dorsal pancreas shown in FIGS. 3B and 3C illustrating a condensing cord of tubulo-acinar cells (arrows)
Figure 3:
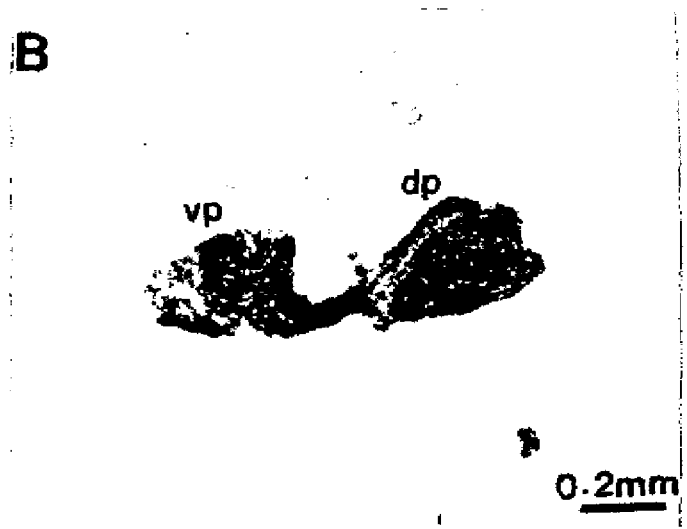
Figure 3:
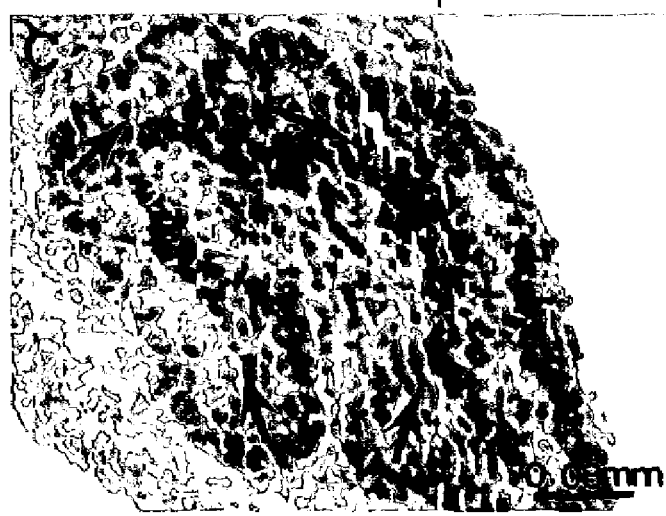

Transplantation of Embyonic Pancreatic Anlagen Results Information of Islets of Langerhans A pancreatic anlage consisting of both dorsal and ventral pancreata was harvested surgically under a dissecting scope from an E12.5 Lewis rat embryo, and suspended in saline solution on ice under sterile conditions (see FIG. 3A). Within 2 hours after removal, the pancreatic anlage was implanted into the omentum of an adult Lewis rat. Two weeks following the implantation, the adult Lewis rat was sacrificed, and the pancreatic transplant was removed for histological analysis. Histological examination of fixed, paraffin-embedded, and sliced sections of the tissue mass stained with hematoxylin and eosin revealed that the transplanted pancreatic anlage has grown and developed into tissue containing islets of Langerhans.

Shown in FIG. 3A is a photograph of a section of duodenum (duo) from an E12.5 Lewis rat embryo. The dorsal pancreas (dp) and ventral pancreas (vp) are labeled. Shown in FIG. 3B is a H&E-stained section the dorsal and ventral pancreatic anlage with the duodenum removed. FIG. 3C is a higher power view of the dorsal and ventral pancreatic anlage shown in 3B.

Figure 4:
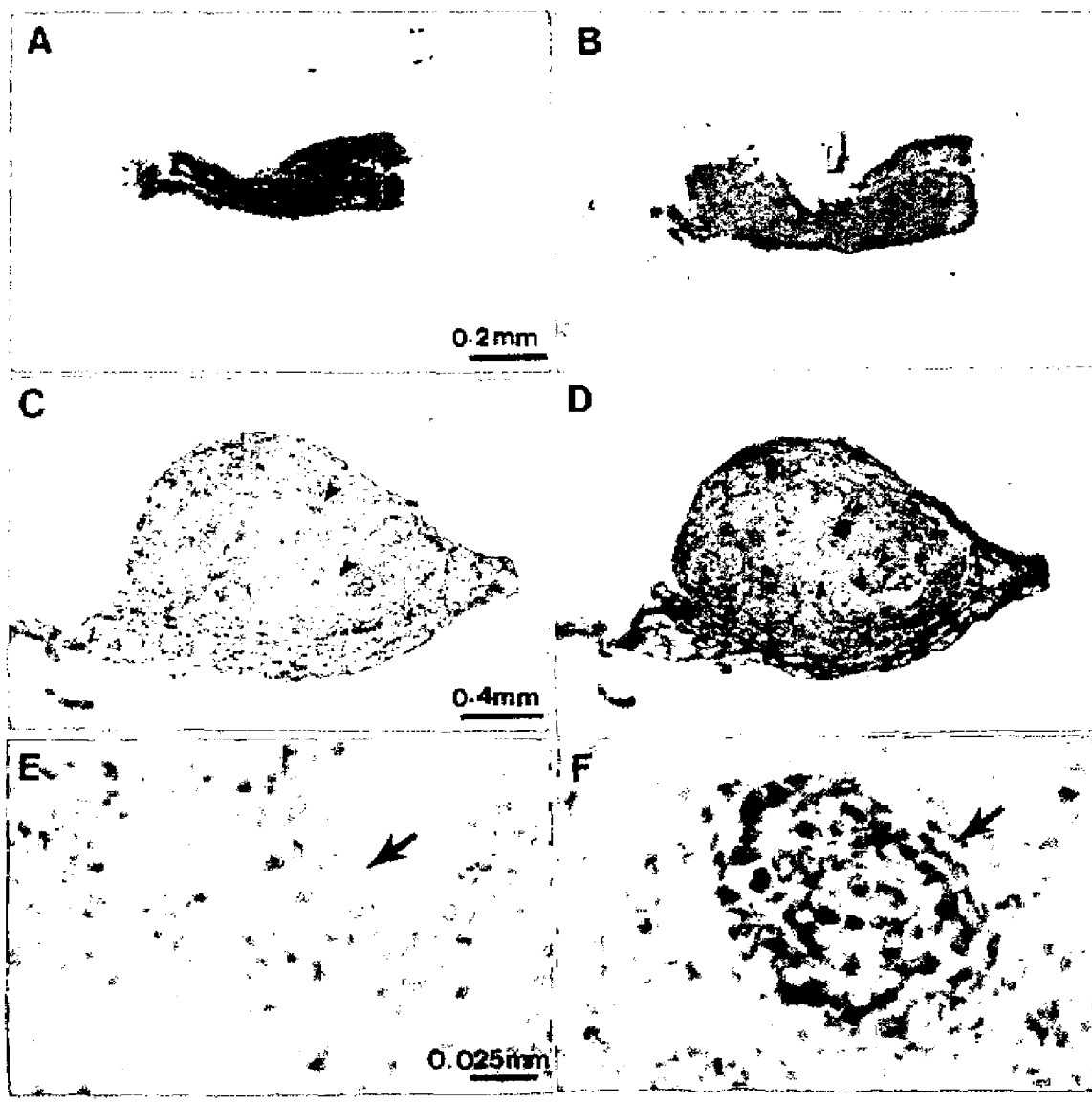
FIG. 4A shows an H&E section of a pancreatic anlage obtained from an E12.5 Lewis rat embryo.
FIG. 4B shows an adjacent section of anlage stained with an anti-insulin antibody indicating no positive staining in the tissue section.
FIGS. 4C through 4F show pancreatic anlagen two weeks post transplantation with 4C and 4E showing control stained sections and 4D and 4F showing staining with anti-insulin antibodies. Arrows delineate islets of Langerhans as positive-staining structures.

To determine whether immunoreactivity for insulin is present at E12.5 in pancreatic anlagen, we performed additional stains. FIG. 4A shows an H & E-stained section of a pancreatic anlage obtained from an E12.5 Lewis rat embryo. FIG. 4B shows an adjacent section stained with an anti-insulin antibody. No positive staining for insulin is detected at E12.5.

By two weeks post-transplantation of whole pancreatic anlagen into the omentum of a Lewis rat, the tissue has undergone differentiation. Shown in FIG. 4C is a control-antibody stained section and in 4D, an adjacent insulin-stained section. Corresponding negative (4C) and positive (4D) tissue is delineated (arrowheads). Shown in 4E is a control-stained section of another transplanted pancreas 2 weeks following implantation and in 4F an adjacent insulin-stained section. An islet of Langerhans is delineated (arrows). Magnifications are shown for A&B (A), for C&D (C) and for E&F (E).

Figure 5:
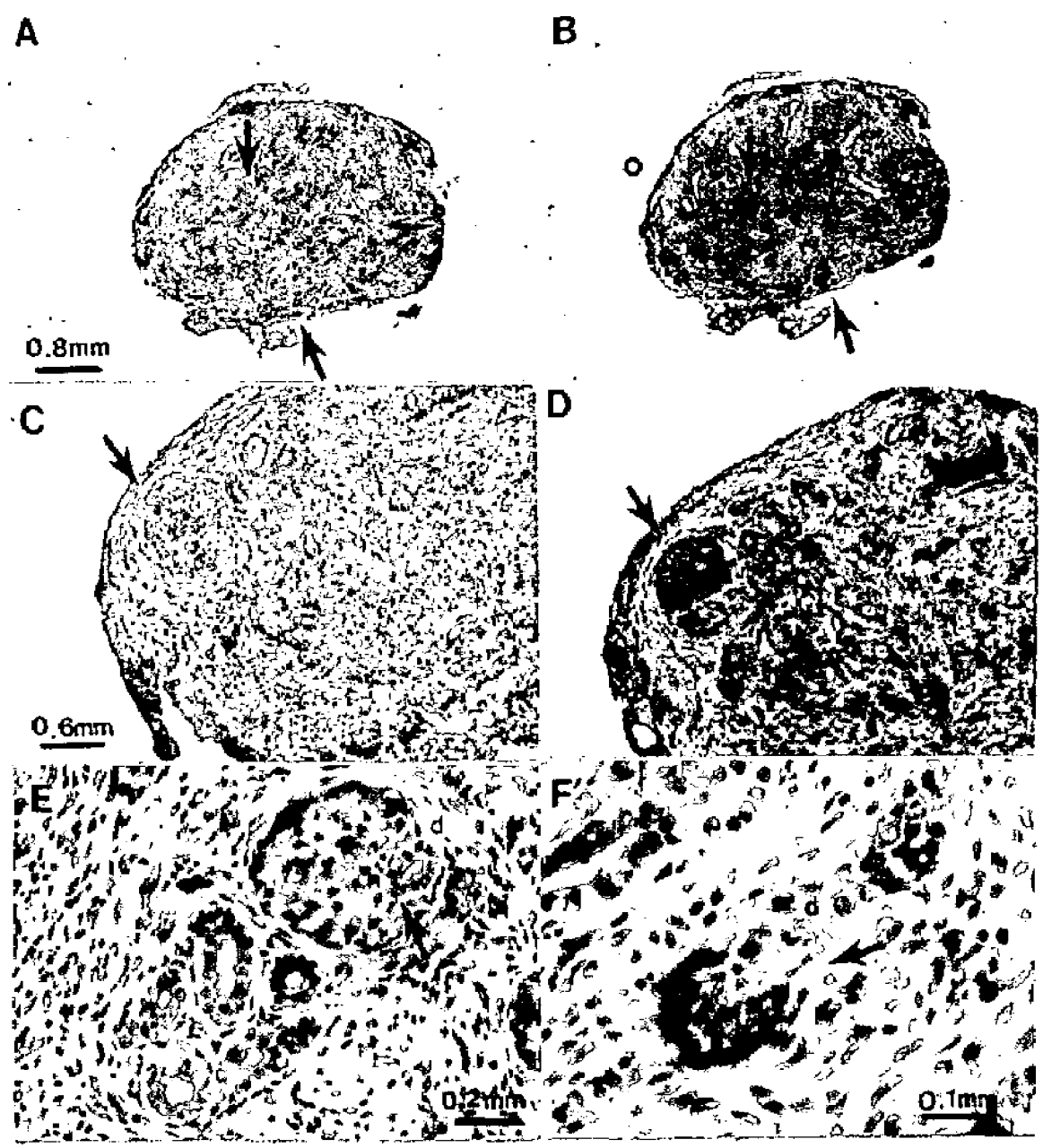
FIG. 5A is a control-antibody-stained section originating from a ventral pancreatic anlage, 6 weeks post-implantation into the peritoneum of an adult Lewis rat. Negative-staining tissue is delineated by arrows.
FIG. 5B is an adjacent section stained with anti-insulin antibody. Arrows delineate islet tissue. The tissue has undergone growth, and more islets are present that at 2 weeks post-transplantation.
FIGS. 5C and 5D are higher-power views of another control antibody stained section and another anti-insulin stained section, respectively.
FIGS. 5E and 5F are tissue sections stained with anti-insulin antibodies in which developing ductal islets that remain to be connected to the duct epithelium are delineated by arrows.

To characterize the growth and development of the pancreas anlagen beyond 2 weeks and the pattern of insulin immunoreactivity, we examined the structures that were present in the host peritoneum 6 or 15 weeks following transplantation of E12.5 pancreatic anlagen. Shown in FIG. 5A is a control-antibody-stained section originating from a pancreatic anlage, 6 weeks post-implantation into the peritoneum of an adult Lewis rat. Shown in FIG. 5B is an adjacent section stained with anti-insulin antibody. Islet tissue is delineated (arrows). Shown in FIGS. 5C and 5D are higher-power views of another control-antibody-stained section (FIG. 5C) and an adjacent section stained with anti-insulin antibody (FIG. 5D). FIGS. 5E-F are sections stained with anti-insulin antibodies in which developing ductal islets that remain connected to the duct epithelium (d) are delineated (arrows). Magnifications are shown for A&B (A), for C & D (C), and for E and F.

Figure 6:
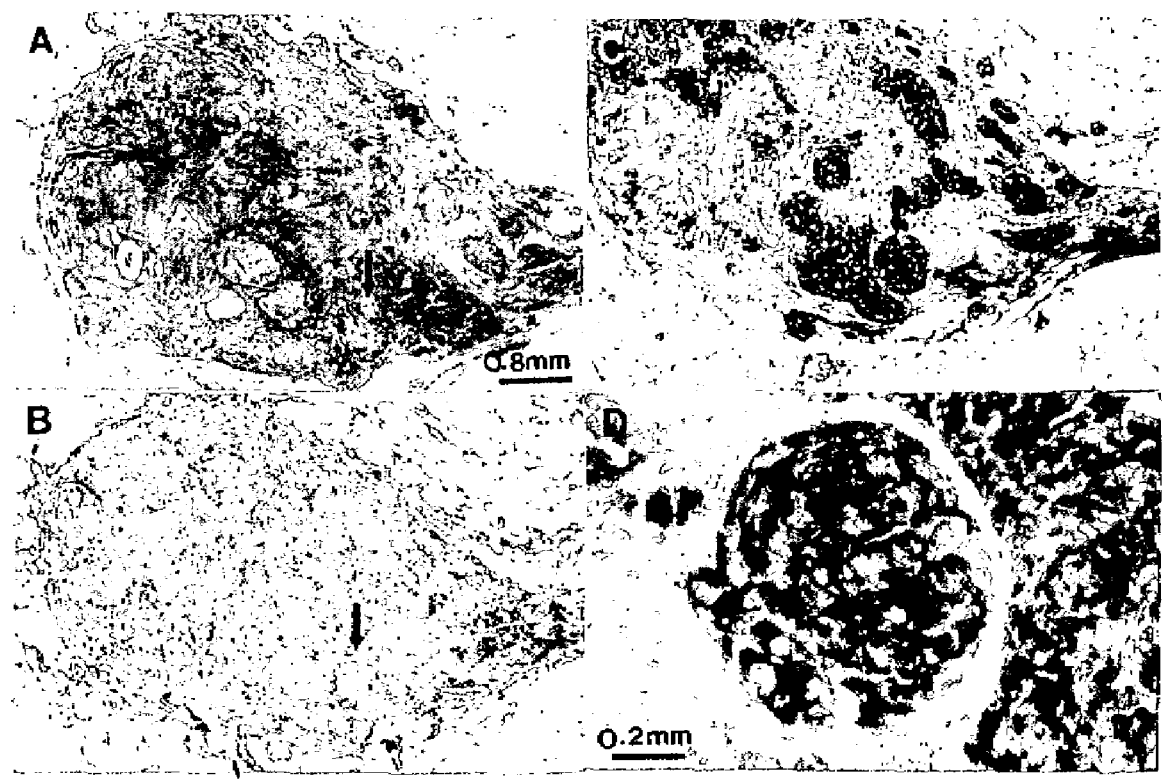
FIG. 6 illustrates a pancreas anlage approximately fifteen weeks post-transplantation showing the chimeric organ structure of islet tissue within stroma surrounded by peritoneal fat with arrows delineating islets.

FIG. 6 illustrates a pancreas anlage 15 weeks post-transplantation. Shown in FIG. 6A is an H& E-stained section and in FIG. 6B, a control serum stained section. The corresponding anti-insulin antibody stained-section is shown in FIG. 6C. FIG. 6D shows an enlarged islet of Langerhans, stained with anti-insulin antibodies. Arrows delineate islets. Magnifications are shown in A for A through C and in D. The 'organ' is a novel one, consisting of islet tissue within stroma surrounded by peritoneal fat. There is no inflammatory reaction in the peritoneum that would suggest active exocrine secretory activity.

The combined Gomori method stains beta cells purple and acinar cells bright pink. Shown in FIG. 7A is a section from a developed pancreatic anlagen 15 weeks post-transplantation. Shown in FIG. 7B is a section of dorsal pancreas from a newborn rat. Islets (arrows) and acinar cells (arrowheads) are delineated. As would be expected, combined Gomori positive (bright pink) acinar tissue is present in FIG. 7B. In contrast, only islet tissue surrounded by non-staining stroma is present in FIG. 7A. Magnifications are shown (B).

Figure 8:
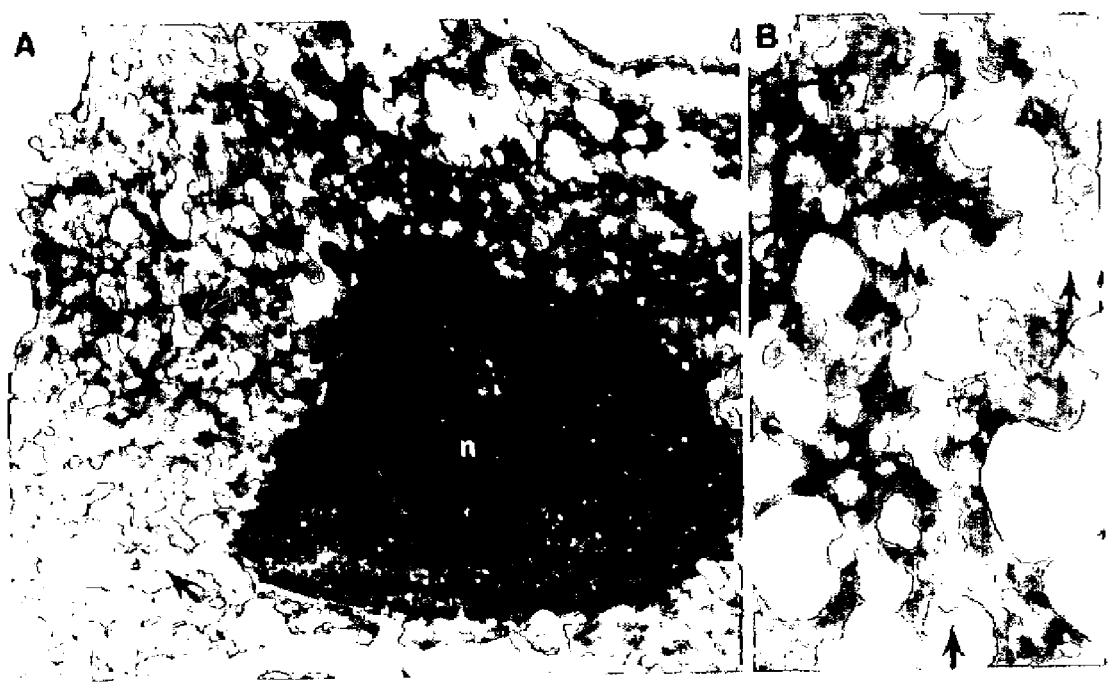
FIGS. 8A shows an electron microscopy image of a cell within an islet, wherein the cell is packed with neurosecratory granules containing eccentric dense cores which represent crystalized insulin (arrows)
FIG. 8B shows a higher magnification of the granules.

Electron microscopy was performed to delineate whether beta cells contained insulin granules. FIG. 8A shows a cell within an islet. Its cytoplasm is packed with neurosecretory granules containing eccentric dense cores which represent crystallized insulin (arrows). A higher magnification of the granules is shown in FIG. 8B.

Figure 9:
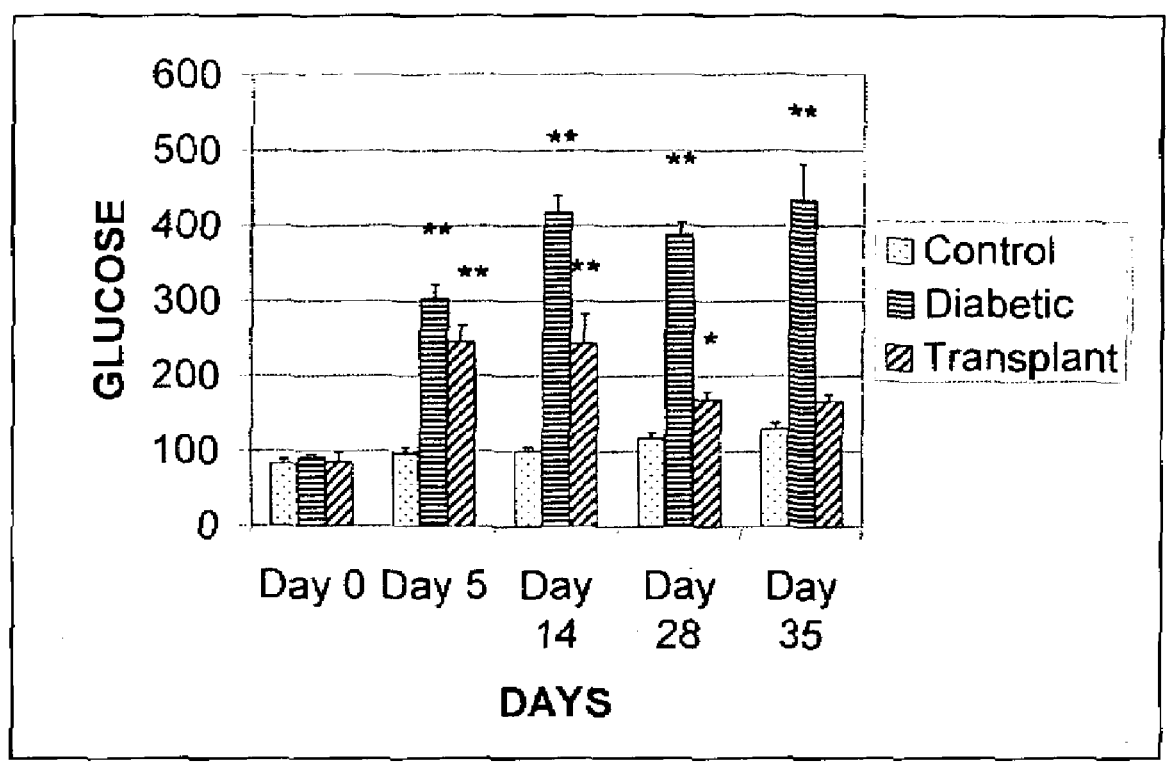
FIG. 9 shows the comparative glucose levels of isotransplanted, non-surgical control, and induced diabetic rats over a thirty-five day period.

Treatment of streptozotocin-diabetes mellitus by transplantation of pancreatic anlagen After measurement of baseline blood glucose levels (day 0), streptozotocin-diabetes was induced in Lewis rats. A control group (control, n=8) received vehicle instead of streptozotocin. On day 5 post-streptozotocin or vehicle, levels of blood glucose were measured. In some streptozotocin diabetic rats, 10 pancreatic anlagen were transplanted into the peritoneum (n=3 transplant). Other rats underwent sham-surgery (N=7 diabetic). Glucose levels were measured again at 8 AM on days 14, 28 and 35-post administration of vehicle or streptozotocin. As shown in FIG. 9, levels of glucose were elevated in diabetic rats compared to controls on days 5, 14, 28, and 35. In contrast, by day 35, glucose levels were not different between controls and transplanted (previously hyperglycemic) rats. **$p<0.01$ vs Control for that day; *$P<0.05$ vs Control for that day, Dunnetts multiple comparison procedure.

Glucose tolerance tests were performed on a second group of control rats (n=6), diabetic rats (n=4) and transplanted (previously hyperglycemic) rats (n=6) at 18 weeks post-transplantation of 10 pancreatic anlagen into the transplanted group, using methodology described in Brown et al, Diabetes 30: 9-13 (1981). Rats were fasted overnight, restrained in a towel wrap, and given D-glucose at a dose of 0.5 g/kg body weight via rapid injection into the tail vein. Blood samples were collected subsequently from the tail vein. The k value for the rate of glucose disappearance (%/min) was determined using 10, 20 and 30 min values. K values (%/min) for glucose disappearance in control rats and in diabetic rats were 2.92±0.44 and 0.48±0.26 respectively, comparable to values reported by Brown et al (control>diabetic, p<0.01). K values for transplanted rats were 2.82±0.46, not significantly different from controls and increased significantly compared to the diabetic animals.

Figure 10:
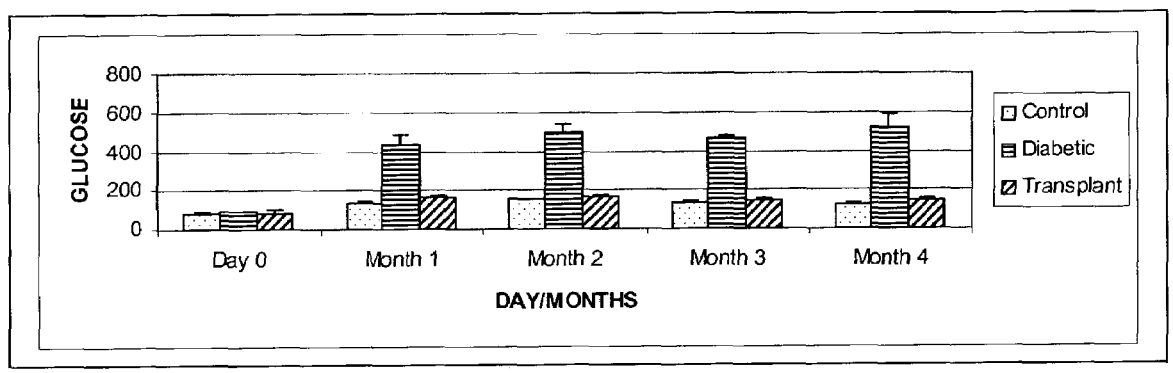
FIG. 10 shows the comparative glucose levels of isotransplanted, non-surgical control, and induced diabetic rats over a four month period.

Glucose level have been measured weekly in the rats used to generate the data shown in FIG. 9. Normoglycemia has persisted for 4 months (16 weeks) (FIG. 10).

Xenotransplantation of Embyonic Pancreatic Anlagen

E 12.5 Lewis rat pancreatic anlagen were transplanted into the omentum of C57B1/6J mice. Some host mice were treated with co-stimulatory blocking agents exactly as before [hCTLA4-Ig: 0.2 mg i.p. on the day of transplantation (day 0); and on days 2 and 4 post-transplantation; anti-CD45RB (Clone 23G2): 0.1 mg i.v. on day 3 prior to transplantation (day −3) through day 0, and 0.1 mg i.p. on days 1-10 post-transplantation; and anti-CD154: 0.25 mg i.p. on days 0, 2 and 4 post -transplantation.] Other mice were treated with injections of vehicle.

Figure 11:
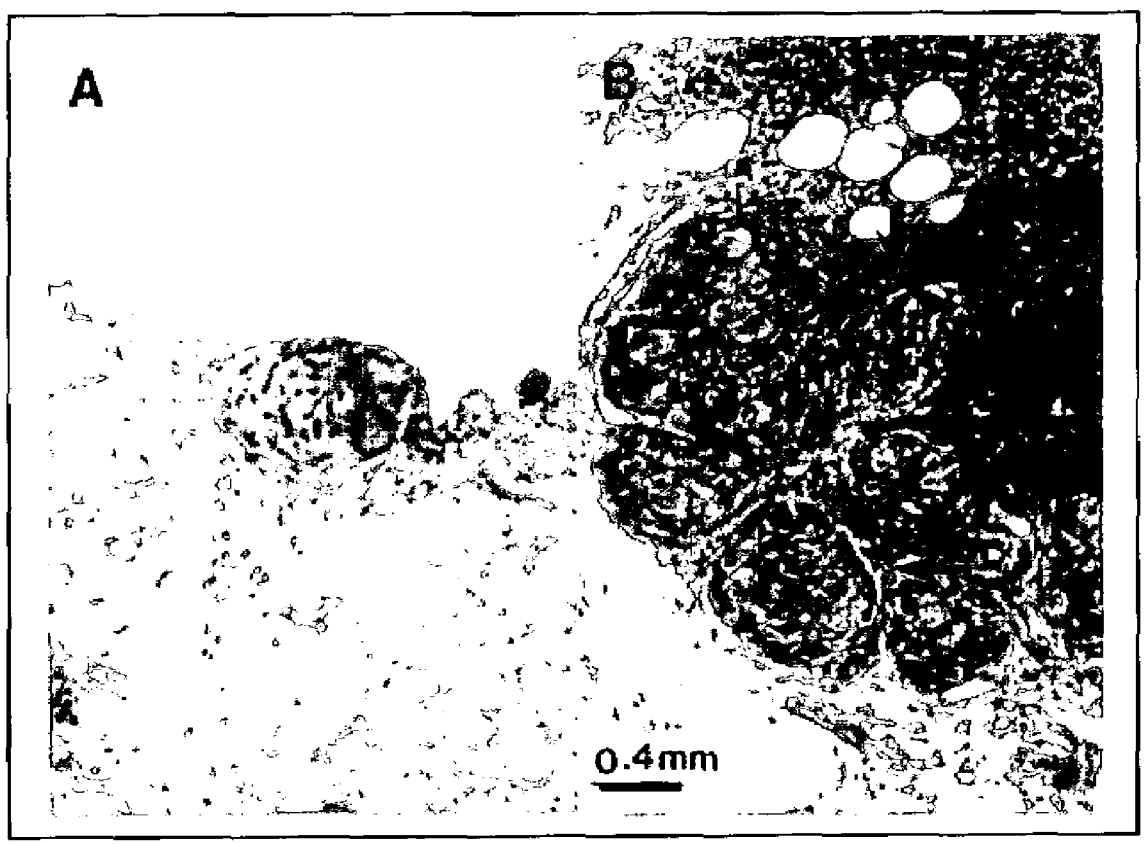
FIG. 11A is a slide showing a cross-section of a xeno-transplanted (rat to vehicle-treated mouse) immature pancreatic tissue, four weeks post-transplant.
FIG. 11B is a slide showing a cross-section of a xeno-transplanted (rat to co-stimulating blockade treated mouse) immature pancreatic tissue, four weeks post-transplant.

FIG. 11A shows a Lewis rat pancreatic anlagen 4 weeks post transplantation into the omentum of a vehicle-treated C57B1/6J mouse. FIG. 11B shows a Lewis rat pancreatic anlagen 4 weeks post transplantation into the omentum of a C57B1/6J mouse that was treated with costimulatory blocking agents. In contrast to the undifferentiated tissue shown in FIG. 11A, islets (arrows) are discernable in FIG. 1B.

Figure 12:
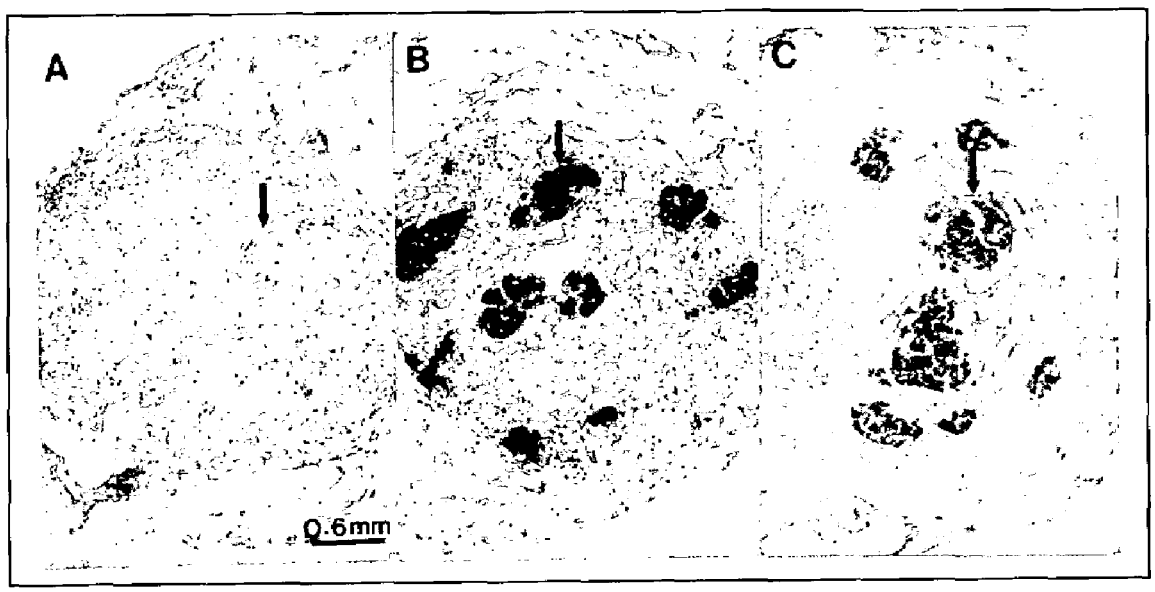
FIG. 12 shows cross-sections of a xeno-transplanted rat pancreas exhibiting different staining protocols.

FIG. 12 shows a second E12.5 Lewis rat pancreas anlagen 4 weeks post-transplantation into the omentum of an adult C57B1/6J mouse that received co-stimulatory blockade. FIG. 12A, control serum; FIG. 12B, anti-insulin antibody; FIG. 12C, combined Gomori stain. Islets are delineated (arrows).

What is claimed is:

1. A method for increasing the pancreatic tissue mass of a mammalian recipient, comprising:
    harvesting immature, substantially non-vascularized pancreatic tissue which is substantially free of antigen-presenting cells from at least one mammalian donor, wherein said tissue comprises at least one non-digested, non-disassociated portion of at least one pancreatic anlage; and
    implanting said tissue into the peritoneal cavity of a mammalian recipient;
    wherein the pancreatic tissue becomes vascularized and mature, thereby developing a functioning chimeric, endocrine pancreas that produces at least insulin in the recipient, thereby increasing the functional pancreatic mass of the recipient.

2. The method of claim 1 wherein the mammalian recipient is a human.

3. The method of claim 2 wherein the mammalian donor is a pig.

4. The method of claim 3 wherein harvesting of said tissue is performed from about day 20 to about day 35 of the gestational period of the donor.

5. The method of claim 2 wherein said tissue is implanted adjacent to a branch of the recipient's superior mesenteric artery.

6. The method of claim 5 wherein said tissue is implanted into a pouch of the donor's omentum.

7. The method of claim 1 wherein said anlage comprises at least a ventral pancreatic anlage.

8. The method of claim 1 wherein said anlage comprises at least a dorsal pancreatic anlage.

9. The method of claim 1 wherein said tissue comprises at least one whole pancreata.

10. The method of claim 1 further comprising the step of administering at least one immunosuppression composition to the recipient to reduce the chance of rejection of said tissue by said recipient.

11. The method of claim 1 further comprising the step of administering at least one co-stimulatory blockade composition to said recipient to reduce the chance of rejection of said tissue by said recipient.

12. The method of claim 1 further comprising the step of treating said tissue with at least one growth factor to enhance the post-implantation growth and development of the tissue.

13. The method of claim 1 wherein the immature pancreatic tissue is harvested from the at least one mammalian donor before dorsal anlage and ventral anlage of the pancreas of the donor become fused.

14. A method for treating diabetes in a mammalian recipient in need of such treatment, comprising:

harvesting immature, substantially non-vascularized pancreatic tissue which is substantially free of antigen-presenting cells from at least one mammalian donor, wherein said tissue comprises at least one non-digested, non-disassociated portion of at least one pancreatic anlage; and implanting said tissue into the peritoneal cavity of a mammalian recipient;

wherein the pancreatic tissue becomes vascularized and mature, thereby developing a functioning chimeric, endocrine pancreas that produces at least insulin in the recipient in an amount sufficient to treat diabetes.

15. The method of claim 14 wherein the immature pancreatic tissue is harvested from the at least one mammalian donor before dorsal anlage and ventral anlage of the pancreas of the donor become fused.

* * * * *

UNITED STATES PATENT AND TRADEMARK OFFICE
CERTIFICATE OF CORRECTION

| | | |
|---|---|---|
| PATENT NO. | : 7,384,630 B2 | Page 1 of 1 |
| APPLICATION NO. | : 10/395552 | |
| DATED | : June 10, 2008 | |
| INVENTOR(S) | : Marc R. Hammerman | |

It is certified that error appears in the above-identified patent and that said Letters Patent is hereby corrected as shown below:

In the claims:
In claim 6, column 13, line 15: replace "donor's" with --recipient's--.

Signed and Sealed this

Fourteenth Day of September, 2010

David J. Kappos
*Director of the United States Patent and Trademark Office*